United States Patent [19]

Dabrowski et al.

[11] Patent Number: 4,676,924
[45] Date of Patent: Jun. 30, 1987

[54] LIQUID CRYSTALLINE ISOTHIOCYANATES WITH DIOXANE RING AND LIQUID CRYSTALLINE ADMIXTURES CONTAINING SAME

[75] Inventors: Roman Dabrowski; Jerzy Dziaduszek; Jaroslaw Szulc; Zygfryd Witkiewicz; Zofia Stolarz; Krystyna Kenig; Gabriela Adamska, all of Warsaw, Poland

[73] Assignee: Wojskowa Akademia Techniczna, Warsaw, Poland

[21] Appl. No.: 749,809

[22] Filed: Jun. 28, 1985

[30] Foreign Application Priority Data

Jul. 2, 1984 [PL] Poland .................................. 248519
Jul. 2, 1984 [PL] Poland .................................. 248520

[51] Int. Cl.$^4$ ...................... C09K 3/34; C09D 319/06
[52] U.S. Cl. ............................. 252/299.61; 252/299.1; 252/299.2; 549/371; 549/372; 549/373
[58] Field of Search ................... 549/371, 372, 373; 252/299.61, 299.1, 299.2

[56] References Cited

U.S. PATENT DOCUMENTS 4,322,354 3/1982 Sorkin .................................. 549/373
4,344,856 8/1982 Demus et al. .................. 252/299.61

FOREIGN PATENT DOCUMENTS 2041354A 9/1980 United Kingdom .

OTHER PUBLICATIONS

Mol. Cryst. Liq. Cryst., vol. 102, (letters), pp. 155–160 4-/Trans-4-n-Alklycycyohixyl/Isothiocyanatobenzenes A New Class of Low–Melting Stable Nematics, R. Dabrowski.

Primary Examiner—Dolph H. Torrence

[57] ABSTRACT

New compounds of the general formula:

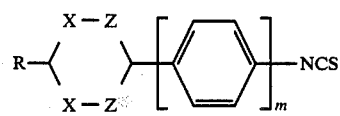

wherein the symbols X stand for carbon atom bonded with two hydrogen atoms /—$CH_2$— group/ and the symbols Z stand for oxygen atom or the symbols X stand for oxygen atom and the symbols Z stand for carbon atom bonded with two hydrogen atoms /—$CH_2$— group/, m is an integer of 1 to 2, R represents an alkyl /$H_{2n+1}C_n$/ or an 4-alkylphenyl /$H_{2n+1}C_n$—$C_6H_4$/ or an alkylbiphenyl /$H_{2n+1}C_n$—$C_6H_4$—$C_6H_4$/ or an alkylcyclohexylphenyl group /$H_{2n+1}C_n$—$C_6H_{10}$—$C_6H_4$/, the term alkyl group signifies an alkyl chain containing 1 to 15 carbon atoms or it also signifies a branched-chain alkyl group $C_2H_5$—CH/$CH_3$/—/$CH_2$/$_k$ where k in an integer of 1 to 3, have utility as liquid crystals. A process for manufacture of compounds of the general formula I. Liquid crystalline admixtures containing those compounds and a way of selection of their compositions to obtain the admixtures which exhibit smectic, smectic and nematic or only smectic properties as well as their use in electro-optical devices is described.

12 Claims, 1 Drawing Figure

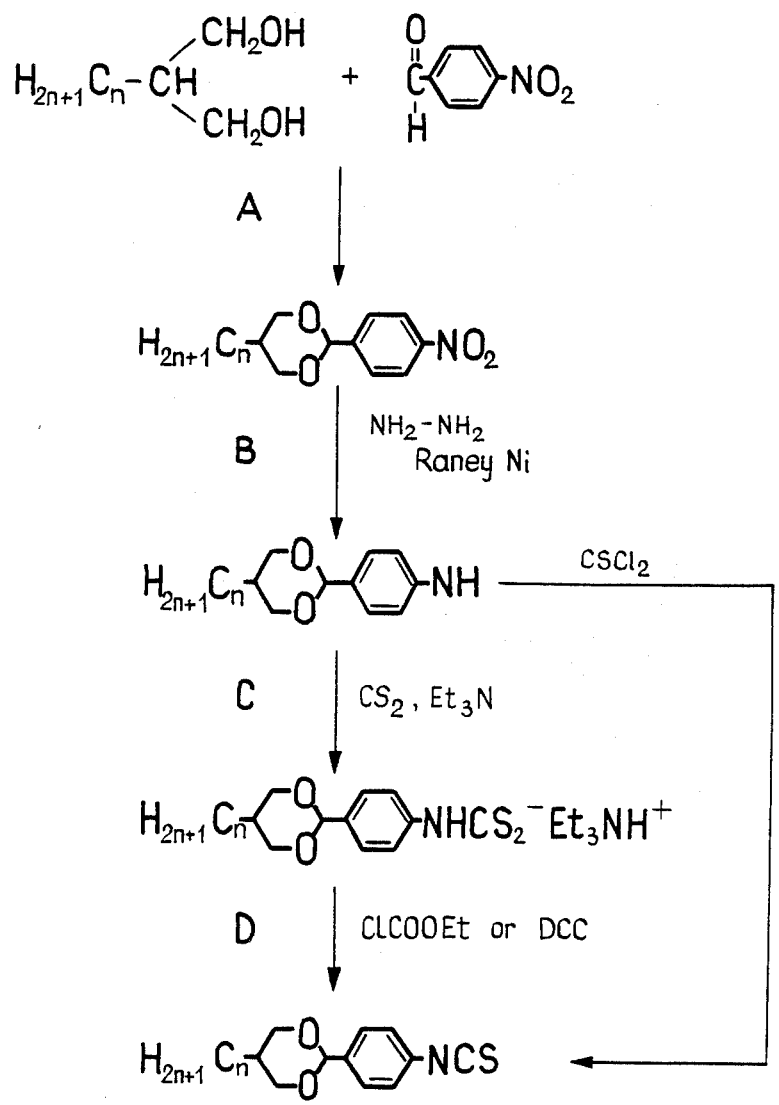
Scheme 1

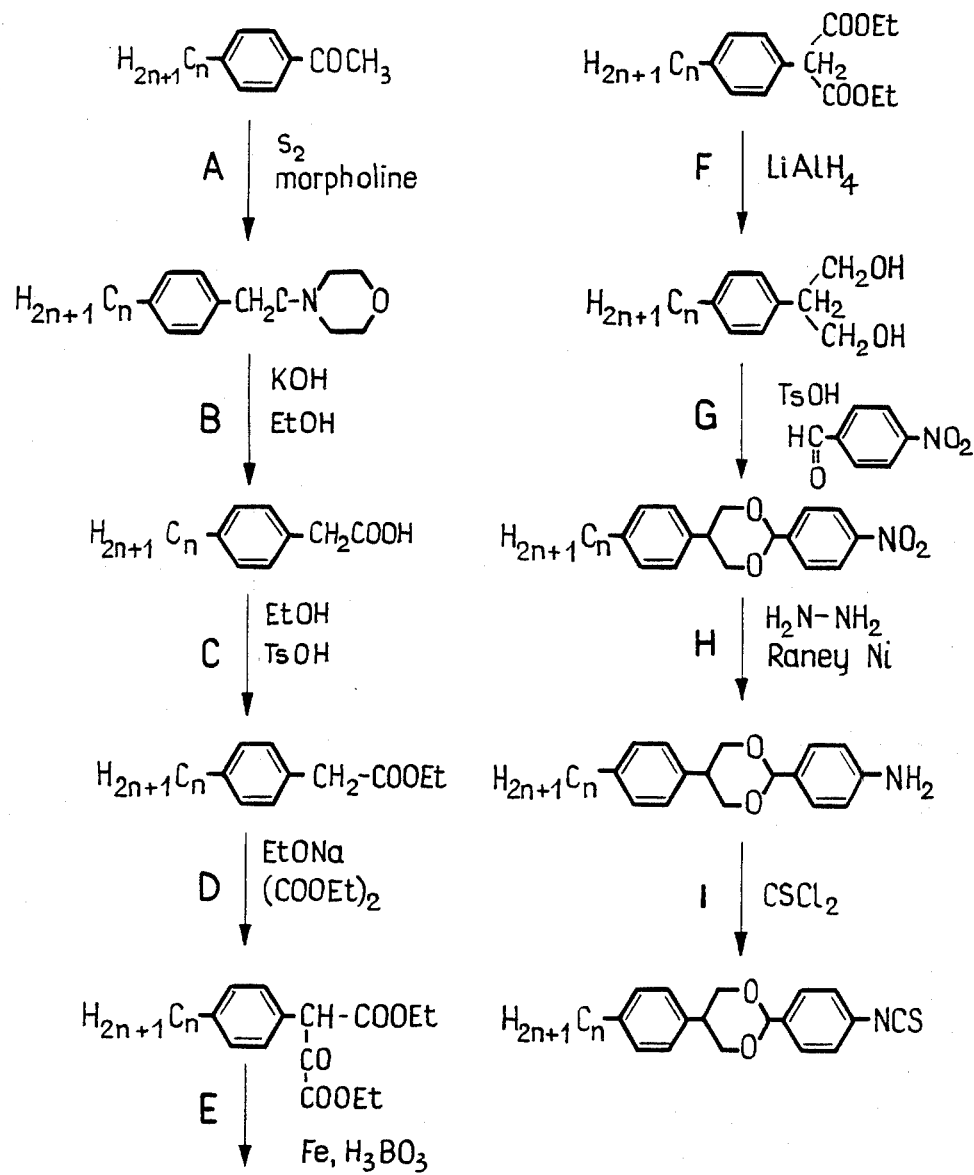
Scheme 2

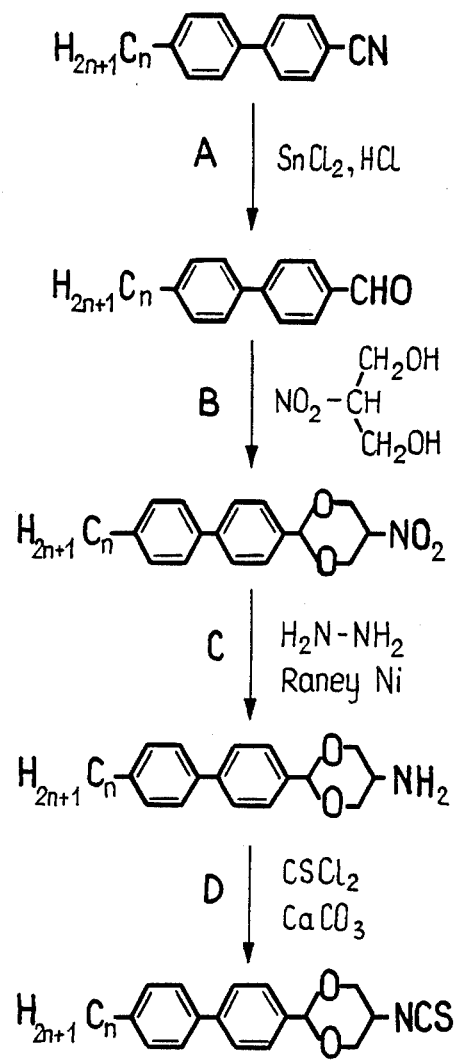
Scheme 3

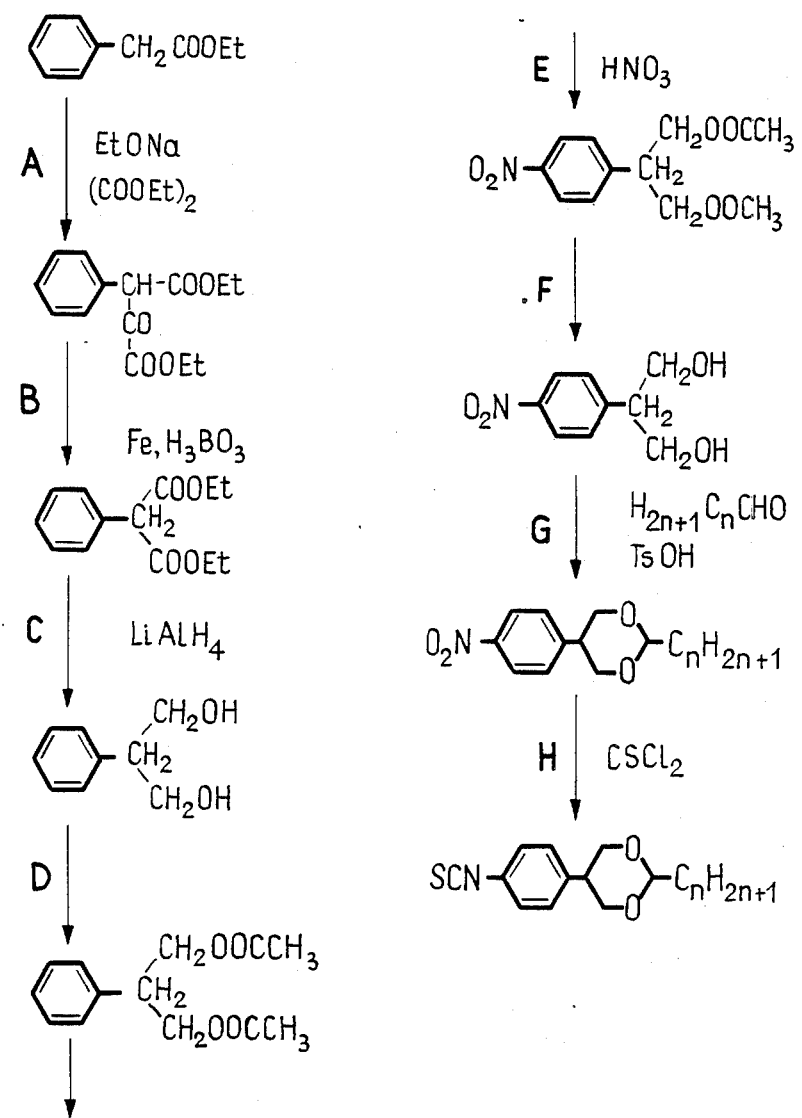
Scheme 4

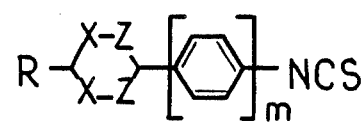
Formula I

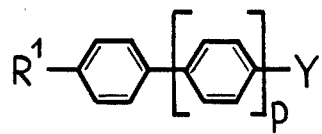
Formula II
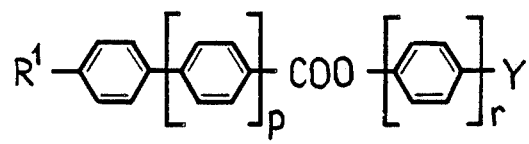
Formula VI
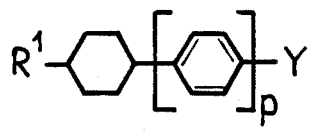
Formula III
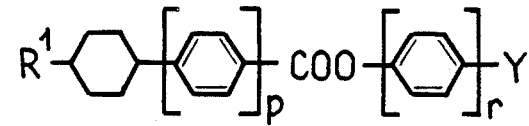
Formula VII
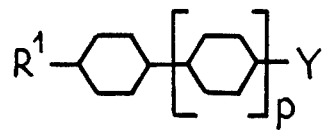
Formula IV
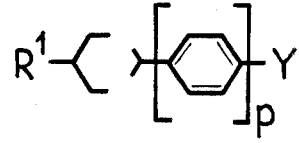
Formula VIII
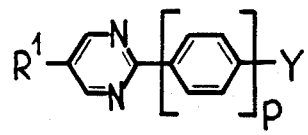
Formula V
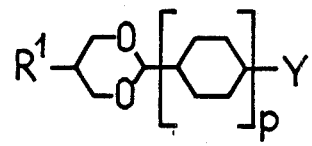
Formula IX

Formula X
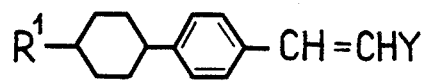
Formula XI
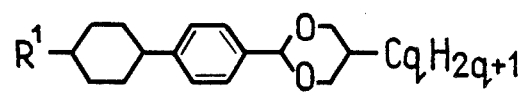
Formula XII
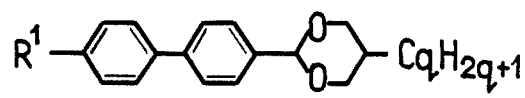
Formula XIII

LIQUID CRYSTALLINE ISOTHIOCYANATES WITH DIOXANE RING AND LIQUID CRYSTALLINE ADMIXTURES CONTAINING SAME

FIELD OF THE INVENTION

The present invention relates to electrooptical displays especially to liquid crystalline admixtures useful in such displays.

DESCRIPION OF THE PRIOR ART

In the liquid crystalline admixtures already known, cyano derivatives of biphenyl (British Pat. No. 1,433,130), cyclohexylbenzene (West German Pat. No. 2,636,684), phenyldioxane (U.S. Pat. No. 4,322,354 and East German Pat. No. 139,852) as well as phenylpyrimidine (West German Pat. No. 2 547 737) are most often used. Only once has the use of isothiocynate derivatives of cyclohexane (out U.S. application Ser. No. 594,860, March 1984, now U.S. Pat. No. 4,528,116) been disclosed.

The compositions useful in displays, e.g. those based on the twisted nematic effect, should have nematic properties, positive dielectric anisotropy, low viscosities, low melting and relatively high clarification points. They also should be resistant to light, heat, humidity and electric fields. Only a limited number of nematic liquid crystal compounds thus far known possesses the characteristics which afford possibilities for obtaining such compositions.

The number of liquid crystalline nematic admixtures in the prior art is additionally limited because so far they might be prepared by mixing compounds having nematic features. Only small amounts of compounds of smectic properties may be added to liquid crystalline nematic substances to avoid a viscosity increase within the lower temperature range of mesophase. The number of admixtures of nematic properties is limited because of limited number of the liquid crystalline nematic compounds for if the length and rigidity of molecule increases, nematogeneous properties are decreased and smectogeneous properties are increased.

There are also known devices utilizing smectic liquid crystalline substances (The Physics and Chemistry of Liquid Crystal Devices, ed. G. J. Sprokel, Plenum Press, New York 1980). Such substances should make possible display operation within the range of temperatures $-10°$ C.-$60°$ C. or wider. Within this temperature range the substance should not crystallize, i.e. should exist as the stabile smectic phase. Furthermore, it is advantageous if the transition from smectic to isotropic phase is separated by the narrow area of the nematic phase because such a feature makes possible the orientation of liquid crystalline layers by electric fields to get homogeneously arranged layers.

It is difficult to make liquid crystalline smectic admixtures both with the wide range of smectic phase and narrow range of nematic one from the compounds known in the prior art.

SUMMARY OF THE INVENTION

According to the present invention there is provided a new group of compounds with characteristics which allow mixture within the group or when mixed with compounds from other groups, which have exclusively smectic or nematic phase or both smectic and nematic phases. In the last case the width of the temperature range of each Phase can be controlled by the components' concentration.

It is worthy of particular notice that these compounds make it possible to obtain nematic admixtures also from compounds having smectic phases. Thus, the number of the available liquid crystalline compounds is increased for practical utilization, and, for the same reason, increases possibility to adjust the physical properties of the liquid crystalline admixtures.

Compounds of the present invention are represented by the formula I:

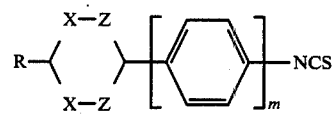

wherein the symbols X stand for oxygen, whereas the symbols Z stand for carbon bonded with two hydrogen atoms /$CH_2$— group/, or the symbols X stand for carbon bonded with two hydrogen atoms /$CH_2$— group/, whereas the symbols Z stand for oxygen, m is an integer of 1, 2 or 0, R represents alkyl /$H_{2n+1}C_n$—/, alkoxy /$H_{2n+1}C_nO$—/, alkanoyloxy /$H_{2n+1}C_nCOO$—/, alkylphenyl /$H_{2n+1}C_n$—$C_6H_5$—/, alkylcyclohexyl /$H_{2n+1}C_n$—$C_6H_{10}$—/, alkylbiphenyl /$H_{2n+1}C_n$—$C_6H_4$—$C_6H_4$—/, alkylcyclohexylphenyl /$H_{2n+1}C_n$—$C_6H_{10}$—$C_6H_4$—/ group, respectively, alkyl groups contain from 1 to 15 carbon atoms in the chain, and the chain may be straight or branched one, $C_2H_5CH/CH_3/$—/$CH_2/_k$, k is an integer of 1 to 3.

The compounds of an formula I wherein m=1 and R is the alkyl chain have only the smectics A phase and the nematic phase does not exist even within the narrow range of temperatures, although they contain short alkyl chains at the terminal position.

DESCRIPTION OF PREFERRED EMBODIMENTS

Figure 1:
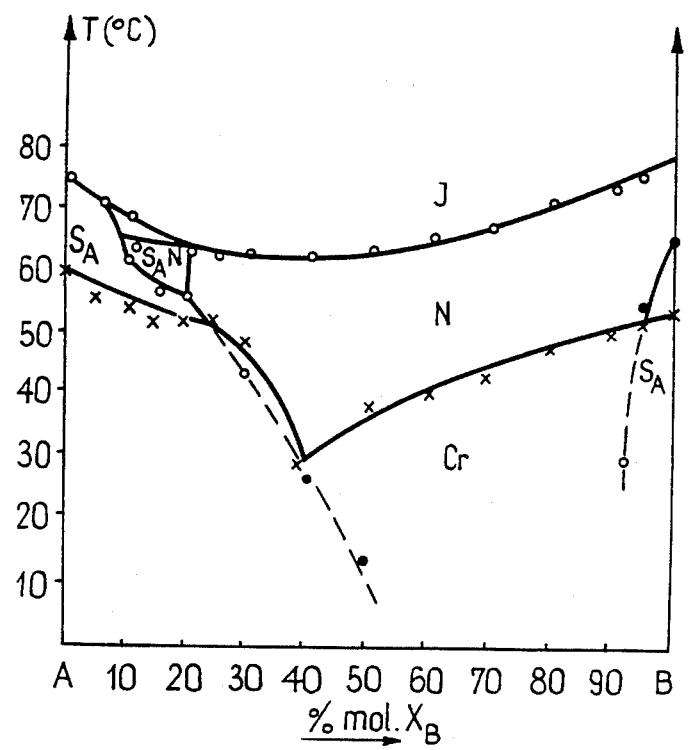

The compounds represented by the formula I of the present invention, wherein R stands for straight or branched alkyl chain, the symbols X stand for carbon atom bonded with two hydrogen atoms methylene groups and Z stand for oxygen atom, whereas m=1, may be prepared as follows:

Scheme 1

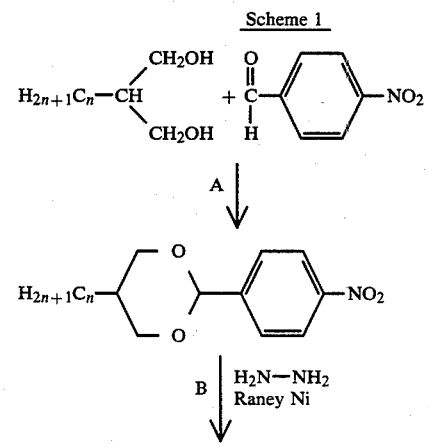

-continued
Scheme 1

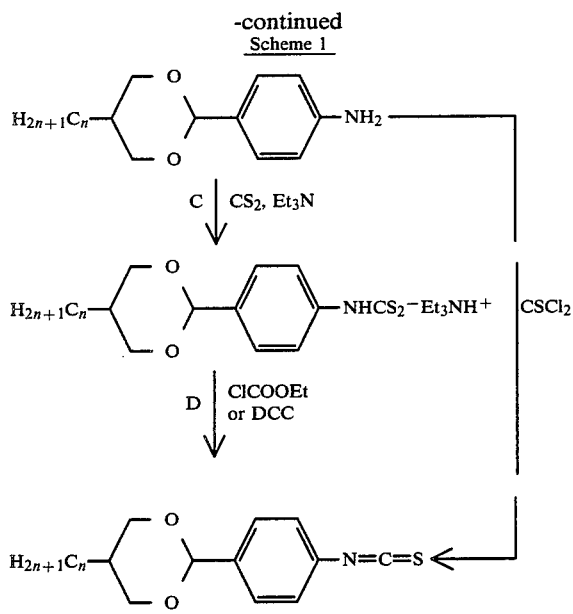

Condensation of p-nitrobenzaldehyde with 2-alkyl-1,3-diol /stage A/ carried out in the presence of small amount of an acid catalyst e.g. toluenesulphonic acid according to the procedure described in J. Prakt. Chem., 323, 902 /1981/. The nitro derivative thus obtained was crystallized and then reduced to 5-n-alkyl-2-/4'-aminophenyl/-1,3-dioxane advantageously by means of hydrazine in the presence of Raney nickel. Then 5-n-alkyl-2-/4'-aminophenyl/-1,3-dioxane dissolved in the mixture of organic solvents was treated with carbon disulphide in the presence of a base e.g. tertiary amine. Dithiocarbamate triethylammonium salt thus prepared was then converted by the action of ethyl or methyl chloroformate or dicyclohexylcarbodiimide /DCC/ into the isothiocyanate derivative which was separated and purified by the crystallization. There is also a useful one-stage convertion of 5-n-alkyl-2-/4'-aminophenyl/-1,3-dioxane into isothiocyanate by the action of thiophosgene in the presence of an alkaline salt e.g. calcium or sodium carbonate.

The 5-n-alkyl-2-/4'-isothiocyanatophenyl/-1,3-dioxanes thus obtained have trans structures and they are colourless compounds exhibiting the smectic $A_1$ phase which is characterised by the quite high transition temperatures from liquid crystalline to isotropic phase. $S_A \rightarrow I$ clarification points observed in this homologous series are higher by 30°–40° C. from those $N \rightarrow I$ points of an analogous series of the dioxane derivatives containing a cyano group /U.S. Pat. No. 4,322,354/ which are nematics. Compound containg a hexyl group shows particularly advantageous properties. It melts at 35° C. to give the smectic $A_1$ phase and turns into the isotropic liquid at 78° C. Phase transition temperatures of prepared compounds according to scheme 1 are listed in the table below, in which symbols Cr, $S_A$, I represent respectively: Cr—crystalline phase, $S_{A1}$—monolayer smectic A phase of, I—isotropic phase. Monotropic transition are given in parentheses.

| No | R | m | X | Z | Cr | $S_{A1}$ | I |
|---|---|---|---|---|---|---|---|
| 1 | $C_2H_5$ | 1 | $CH_2$ | 0 | . 74.0 | ./54.0/ | . |
| 2 | $n-C_3H_7$ | 1 | $CH_2$ | 0 | . 79.0 | ./65.0/ | . |
| 3 | $n-C_4H_9$ | 1 | $CH_2$ | 0 | . 60.0 | . 75.0 | . |
| 4 | $n-C_5H_{11}$ | 1 | $CH_2$ | 0 | . 60.0 | . 79.0 | . |
| 5 | $C_2H_5CH/CH_3/CH_2$ | 1 | $CH_2$ | 0 | . 53.5 | ./47.5/ | . |
| 6 | $n-C_6H_{13}$ | 1 | $CH_2$ | 0 | . 35.0 | . 79.0 | . |
| 7 | $n-C_7H_{15}$ | 1 | $CH_2$ | 0 | . 51.5 | . 81.5 | . |
| 8 | $n-C_8H_{17}$ | 1 | $CH_2$ | 0 | . 47.0 | . 81.5 | . |
| 9 | $n-C_9H_{19}$ | 1 | $CH_2$ | 0 | . 57.0 | . 81.0 | . |
| 10 | $n-C_{10}H_{21}$ | 1 | $CH_2$ | 0 | . 61.0 | . 79.5 | . |
| 11 | $n-C_{12}H_{25}$ | 1 | $CH_2$ | 0 | . 70.5 | . 78.0 | . |

The following details are enclosed to illustrate rather than to limit the invention.

EXAMPLE 1

5-trans-n-butyl-2-/4'-isothiocyanatophenyl/-1,3-dioxane

A. 5-trans-n-butyl-2-/4'-nitrophenyl/-1,3-dioxane

The mixture of 500 ml of benzene, 52.8 g /0.4 mole/ of 2-n-butyl-1,3-propandiol, 66.4 g /0.44 mole/ of 4-nitrobenzaldehyde and 2 g of p-toluenesulphonic acid was refluxed in a round-bottomed flask equipped with a reflux condenser and azeotropic set until water was removed. Then the flask content was placed in a separatory funnel, washed with 2% solution of sodium bicarbonate and dried over $MgSO_4$. Benzene was then distilled off and a residue crystallized from methanol yielding 65.5 g /64%/ of 5-trans-n-butyl-2-/4'-nitrophenyl/-1,3-dioxane of m.p. 50° C. and purity more than 98% of trans isomer.

B. 5-trans-n-butyl-2-/4'-aminophenyl/-1,3-dioxane

To a flask the following was placed: 400 ml of 96% ethanol, 31.2 g /0.5 mole/ of 80% hydrazine hydrate, 53 g /0.2 mole/ of 5-trans-n-butyl-2-/4'-nitrophenyl/-1,3-dioxane 98% pure and m.p. 50° C. The mixture was then heated to 40° C. and Raney nickel was added in portions waiting a moment after a portion has been added until the stormy evolution of gases ceased. Then the reaction mixture was heated for one hour, filtered while hot from nickel and the filtrate was evaporated up to the volume of 100 ml. On cooling at −10° C. the solid was precipitated and filtered off. The yield is 39 g /83%/ of 5-trans-n-butyl-2-/4'-aminophenyl/-1,3-dioxane of m.p. 85°–89° C.

C. D. 5-trans-n-butyl-2-/4'-isothiocyanatophenyl/-1,3-dioxane 23.5 g /0.1 mole/ of 5-trans-n-butyl-2-/4'-aminophenyl/-1,3-dioxane was dissolved in 400 ml of benzene, then placed in 0.5 l Erlenmayer flask, diluted with 50 ml of hexane and 28 ml /0.2 mole/ of anhydrous triethylamine and 12.1 ml /0.2 mole/ of carbon disulphide was added. The components were thoroughly stirred and the whole placed in refrigerator for two or three days. The precipitated yellow crystals of triethylammonium dithiocarbaminate was filtered off, washed with dry ether and dried on air. The product was then dissolved in 150 ml of chloroform and 21 ml /0.15 mole/ of triethylamine was added then cooled to 0° C. stirring and 14.1 g /0.15 mole/ of methyl chloroformate was added dropwise. Stirring was continued for one hour than the reaction mixture was placed in the separatory funnel and washed with 200 ml 3N hydrochloric acid and twice with water. After layers has been separated chloroform solution was dried over $MgSO_4$. Chloroform was removed by evaporation and residue was crystallized from methanol and then from n-hexane heating the solution with small amount silicagel required for the decolourization. The yield 8.6 g /31%/ of 5-trans-n-butyl-2-/4'-isothiocyanatophenyl/-1,3-dioxane showing transition temperature from solid to smectic $A_1$ phase /$T_{Cr \to S_{A1}}$/ 60° C. and transition temperature from smectic to isotropic phase /$T_{S_{A_1} \to I}$/ 75° C.

EXAMPLE 2

5-trans-n-hexyl-2-/4'-isothiocyanatophenyl/-1,3-dioxane

Starting from 26.3 g /0.1 mole/ of 5-trans-n-hexyl-2-/4'-aminophenyl/-1,3-dioxane and following the analogous procedure as described in the example 1 12.2 g /40% yield/ of 5-trans-n-hexyl-2-/4'-isothiocyanatophenyl/-1,3-dioxane was obtained which is characterised by the following phase transition: Cr 35 $S_{A1}$ 79 I. In the similar manner one can prepare other compounds of the formula I wherein m=1, X=$CH_2$, Z=O. There transition temperatures are listed in the table.

EXAMPLE 3

5-trans-n-hexyl-2-/4'-isothiocyanatophenyl/-1,3-dioxane

In a 200 ml three-neck round-bottom flask the following was placed: 40 ml of water, 6 g /0.06 mole/ of calcium carbonate, 20 ml of chloroform and 5.2 g /0.046 mole/ of thiophosgene. The reaction mixture was then cooled to 0°-5° C. and vigorously stirring solution of 10.5 g /0.04 mole/ of 5-trans-n-hexyl-2-/4'-aminophenyl/-1,3-dioxane in 40 ml of chloroform was added dropwise maintaining the temperature at 0°-5° C. The mixture was then heated for 1 hour at 35° C. and poured into 50 ml of water. Layers were separated, chloroform solution was washed with 1% hydrochloric acid solution and dried over anhydrous magnesium sulphate. The solution was then filtered through a silica gel layer and evaporated. The residue was crystallized from hexane, boiling with small amount of a silica gel to decolourize, yielded 6.1 g /50%/ 5-trans-n-hexyl-2-/4'-isothiocyanatophenyl/-1,3-dioxane as a white crystalline compound of phse transition temperatures Cr 32 $S_{A1}$ 77 I.

EXAMPLE 4

6.8 g /0.033 mole/ of dicyclohexylcarbodiimide /DCC/ was dissolved in 30 ml of dry ether and to the solution was added as follows: 40 g of carbon disulphide, solution of 7.5 g /0.03 mole/ of optical active 5-trans-/2-methylbutyl/-2-/4'-aminophenyl/-1,3-dioxane in 30 ml of dry ether. The mixture was set aside for dozen or so hours, then the precipitated solid of dicyclohexylurea was filtered off, the filtrate was concentrated, residue dissolved in benzene and filtered through a silica gel. The solution was evaporated to dryness on a Rotovap and the remains crystallized from n-hexane yielding 3.5 g /40%/ of 5-trans-/2-methylbutyl/-2-/4'-isothiocyanatophenyl/-1,3-dioxane of phase transition temperatures Cr 53.5 $S_{A1}$ /47.5/ I.

The compounds of the formula I of the present invention, wherein R is alkylphenyl group /R=$H_{2n+1}C_n$—$C_6H_4$—/; Symbols X stand for carbon atom bonded with two hydrogen atoms, symbols Z for oxygen atom and m=1 may be prepared according to the following scheme:

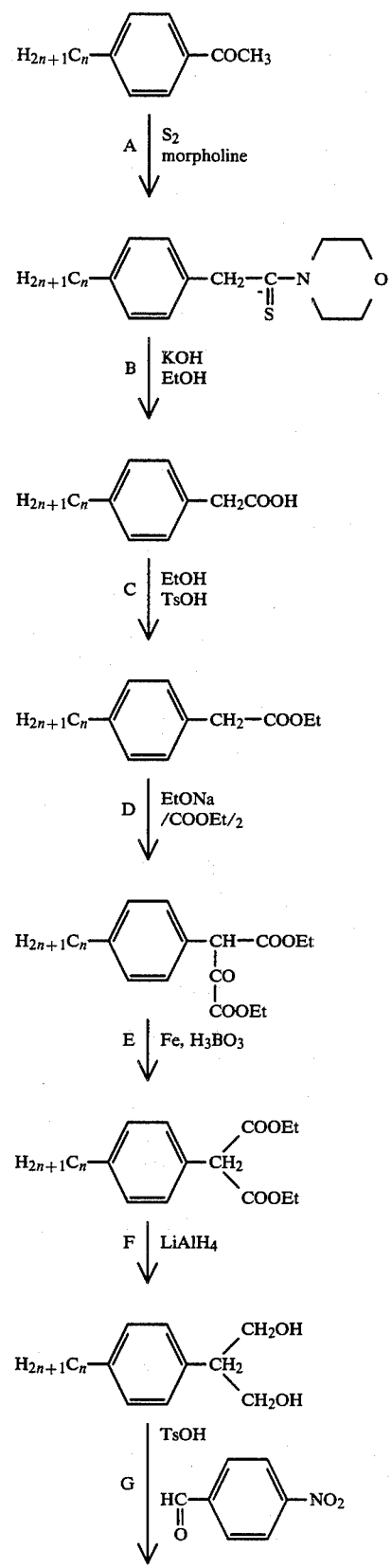

Scheme 2

-continued
Scheme 2

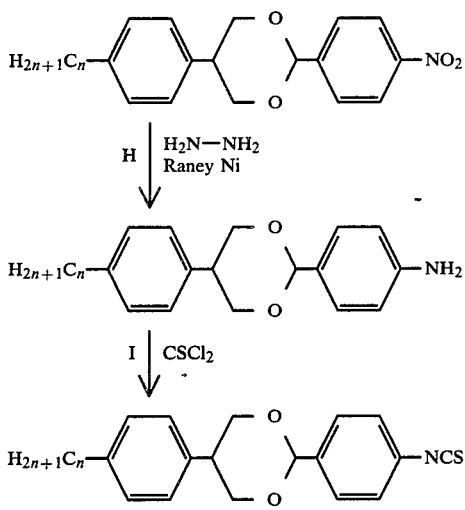

The following additional examples are enclosed rather to illustrate than to limit the invention:

EXAMPLE 5

5-trans-/4'-n-propylphenyl/-2-/4"-isothiocyanato-phenyl/-1,3-dioxane Ethyl-4-n-propylphenylacetate A. In a three-neck 0.5 l round-bottomed flask equipped with a stirrer, a thermometer and a reflux condenser the following was placed: 146 g /0.9 mole/ of 4-n-propylacetophenone, 57.6 g /1.8 mole/ of sulphur and 156.6 g /1.8 mole/ of morpholine. The mixture was stirred and refluxed /at about 110° C./ for 11 hours. Then the flask was cooled, and the content poured into a 1 l control flask in which 360 ml of methanol was placed. The solution was then cooled to 0° C. The thiomorpholide crystals was filtered off, washed with cooled methanol. The crude product melts at 60°–65° C. and was subjected without drying to hydrolysis reaction.

B. For this purpose to a 2 l one-neck round-bottomed flask the following is added: 600 g 50% solution of KOH, thiomorpholide of 4-n-propylphenylacetic acid obtained in the stage A, 1050 ml of ethanol, and the whole was refluxed for 6 hours. Then 950 ml of ethanol was removed by distillation, the solution was cooled filtered off, and the filtrate acidified with hydrochloric acid to pH=1.

The precipitated crude 4-n-propylphenylacetic acid was filtered off washed with cold water. The crude product was then used without drying in the next stage C to prepare the ester.

C. In 1 l round-bottomed flask the following was placed: The crude 4-propylphenylacetic acid obtained in the stage B, 5.0 g of p-to-luenosulphonic acid, 250 ml of ethanol and 70 ml of benzene. 30 cm Vigreux column was attached with distillation head on a top of it. The mixture was then boiled till water was removed. Benzene and partly alcohol was then distilled off. The residue was boiled under a reflux condenser with an active charcoal filtered and the filtrate was concentrated. The residue was dissolved in n-hexane, filtered through a silica gel layer, and the hexane was then distilled off on a Rotovap, and the remains was distilled under reduced pressure collecting the fractions: I up to 94° C. and II at 94° C. /p=0.2 mm Hg. The yield 92 g of the second fraction /49.8% of theoretical yield on 4-propylacetophenone/ of 97% purity as shown by GC-analysis. Diethyl 4-n-propylphenylmalonate.

D. In a four-necked 1 l round-bottomed flask equipped with a stirrer, a thermometer, a dropping funnel and a reflux condenser protected against moisture by means of tube with anhydrous calcium chloride: 10.3 g /0.447 mole/ of sodium ives placed and 447 ml of an absolute alcohol was dropped carefully. Then to the solution of sodium alcoholate the mixture of 65 g /0.447 mole/ of diethyl oxalate and 92 g /0.447 mole/ of ethyl 4-n-propylphenylacetate was added dropwise with stirring. Stirring was continued for 5 hours. The content of flask was then acidified with 33.5 g of 80% acetic acid /0.447 mole/ and poured onto 1.5 l water with some ice. The mixture was extracted three time with benzene. The combined benzene extracts were washed twice with water and dried over anhydrous magnesium sulphate. Benzene was distilled of on a Rotovap and the crude ethyl ester of 4-n-propylphenylcarboetoxypyroracemic acid was subjected to the decarbonisation reaction.

E. For this purpose an apparatus for vacuum distillation was set and then the crude ethyl ester of 4-n-propylphenylcarboetoxypyroracemic acid with small amount powdered iron and boric acid /a pinch/ was carefully heated up to the temperature 160°–170° C. under reduced pressure of 25 mm Hg /water pump/. Vigorous evolution of $CO_2$ took place at that temperature and pressure increased up to 160-170 mm Hg. After the decarbonisation reaction has been completed the whole was maintained at 170°–175° C. for a period of time and the residue was distilled under reduced pressure yielding 114 g of the crude product. The crude product was then redestilled /p=0.2 mm Hg/ and the following fractions were collected: I 30°–80° C., II 88°–140° C., III 140° C.

I fraction consisted mainly of unreacted diethyl oxalate with ethyl 4-n-propylphenylacetate, II fraction consisted of unreacted ethyl 4-n-propylphenylacetate with a few percent of diethyl propylphenylmalonate, III fraction consisted of 92% diethyl 4-n-propylphenylmalonate. Finally, 62.5 g of diethyl 4-n-propylphenylmalonate was obtained /50% theoretical yield/. 2-/4-n-propylphenyl/propanediol-1,3.

F. 9.5 g /0.14 mole/ of $LiAlH_4$ in 350 ml of anhydrous ether was placed in 1 l flask. A slow stream of nitrogen was passed through the solution of 56 g /0.2 mole/ of diethyl 4-n-propylphenylmalonate in 50 ml of ether was dropped very quickly stirring and cooling the flask on water-both. After the whole diethyl 4-n-propylphenylmalonate has been dropped /about 30 min./ the mixture was then refluxed for 1 hour. Then the reaction mixture was cooled and 8 g /0.09 mole/ of ethyl acetate was added dropwise /to decompose the excess of $LiAlH_4$/. 40 ml of cold water and the solution of 15% sulphuric acid was then carefully dropped with cooling to dissolve precipitated hydroxyoxides. The ether and water layers were separated, the water layer was extracted with ether the combined ether solutions were washed with water and dried over anhydrous magnesium sulphate. After typical workup crude 2-/4-n-propylphenyl/propanediol-1,3 was crystallized from n-hexane /200 ml/. The yield was 29 g /74%/ of 2-/4-n-propylphenylpropanediol-1,3 which melts at 83°–86° C.

5-trans-/4'-n-propylphenyl/-2-/4"-nitrophenyl/-1,3-dioxane.

G. To a 0.5 l round-bottomed flask the following was added: 25 g /0.13 mole/ of 2-/4-n-propylphenyl/-propanediol-1,3, 21.4 g /0.14 l mole/ of 4-nitrobenzaldehyde, about 0.5 g of 4-toluenesulphonic acid and about 200 ml of benzene. The mixture was then refluxed with azeotropic set until all water was removed. The cold reaction mixture was placed in a separatory funnel and washed succesively with water, sodium bicarbonate solution again with water and dried with anhydrous magnesium sulphate. After benzene has been distilled off residue was crystallized from MeOH:THF=600:150 ml yielding 20 g /42%/ of 2-/4'-nitrophenyl/-5-/4"-propylphenyl/-1,3-dioxane of m.p. 140°–142° C.

H. 5-trans-/4'-n-propylphenyl/-2-/4"-aminophenyl/-1,3-dioxane.

In a three-necked 1 l round-bottomed flask the following was placed: 18 g /0.055 mole/ of 2-/4'-nitrophenyl/-5-/4"-propylphenyl/-1,3-dioxane, 7 g /0.138 mole/ of 100% hydrazine hydrate and 300 ml of methanol. The flask content was heated to 40° C. with stirring and a portion of Raney nickel was added at that temperature. Raney nickel was then added in portions until the temperature ceased to rise. The reaction mixture was then refluxed for one hour and filtered off from Raney nickel while hot. On cooling 5-trans-/4'-propylphenyl/-2-/4"-aminophenyl/-1,3-dioxane crystallized from the filtrate yielding 14 g /85.7%/ which melts at 102°–103° C. with decomposition.

I. 5-trans-/4'-propylphenyl/-2-/4"-isothiocyanatophenyl/-1,3-dioxane.

In a three-necked 350 ml flask the following were placed: 5.06 g /5.06. $10^{-2}$ mole/ of $CaCO_3$, 70 ml of chloroform, 70 ml of water, 4.45 g /0.04 mole/ of thiophosgene. While stirring the solution of 10 g /0.034 mole/ of 5-trans-/4'-propylphenyl/-2-/4"-aminophenyl/-1,3-dioxane in 60 ml of chloroform was added dropwise at room temperature for 2 hours. Stirring was then continued for further 2 hours until thiophosgene disappeared. The reaction mixture was poured into about 300 ml of water, thoroughly stirred and filtered through the active carbon layer. The chloroform layer was separated from that of water, washed with diluted hydrochloric acid, water and then dried. Chloroform was distilled off and the remains were crystallized three time from hexane to yield 4.5 g /39.4%/ of 5-trans-/4'-n-propylphenyl/-2-/4"-isothiocyanatophenyl/-1,3-dioxane. This colourless compound was phase transition temperatures Cr 108 $S_E$ 127.5N 169 I.

EXAMPLE 6

5-trans-/4'-n-pentylphenyl/-2-/4"-isothiocyanatophenyl/-1,3-dioxane

This compound was prepared according to the procedure described in Example 5. The phase transition temperature Cr 124N 136 I.

The compounds of the formula I of the present invention, wherein the symbol R stands for alkylcyclohexylphenyl /$H_{2n+1}C_nC_6H_{10}C_6H_4$/ or alkylbiphenyl group /$H_{2n+1}C_nC_6H_4C_6H_4$/, the symbols X stand for oxygen atom and symbols Z stand for carbon atom bonded with two hydrogen atoms, whereas m=0 may be prepared according to the same procedure. This way may be illustrated by the example of the compound with alkylbiphenyl group as follows:

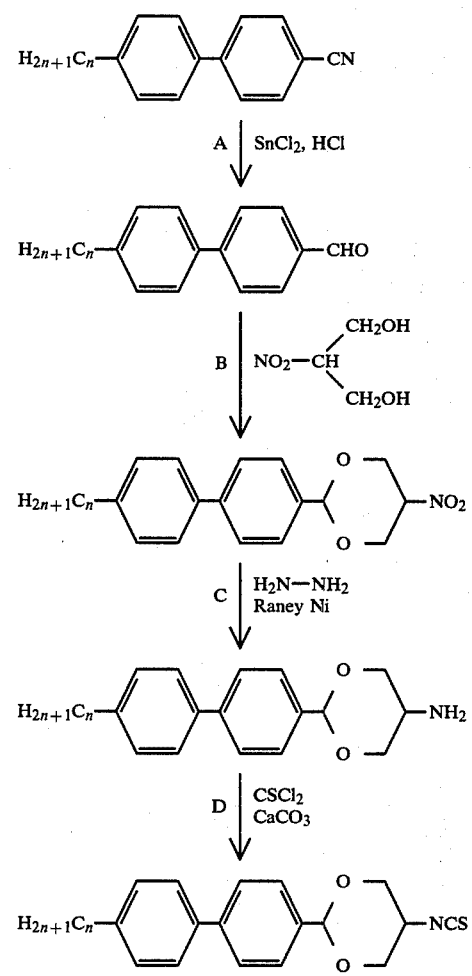

Reduction of 4-alkyl-4'-cyanobiphenyl to aldehyde /stage A/ was carried out according to the procedure described in Mol. Cryst. Liq. Cryst., 87, 109 /1982/ and the thus obtained aldehyde was condensed with 2-nitropropanediol-1,3 refluxing the reaction mixture until whole water was removed by azeotropic distillation. The further stages /CD/ were carried out analogously as described in Example 5.

EXAMPLE 7

2-/4'-ethylbiphenyl/-5-trans-isothiocyanato-1,3-dioxane

Following the preceding scheme 3 the compound of m.p. 55°–58° C. was obtained which was no liquid crystal.

The compounds of the formula I according to the present invention wherein the symbol R stands for alkyl, X for oxygen atom and Z for carbon atom bonded with two hydrogen atoms whereas m=1 may be obtained as follows:

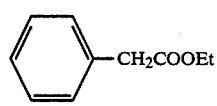

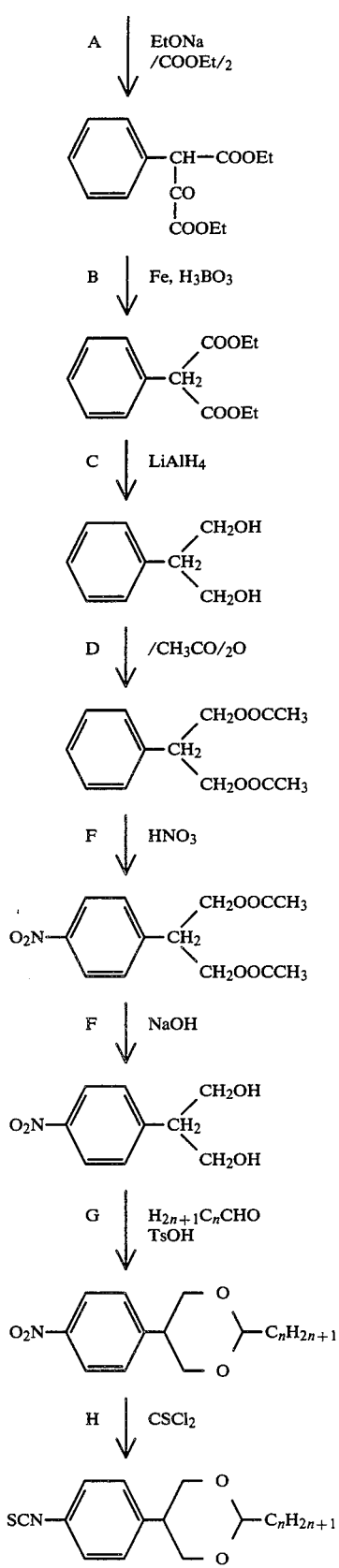

EXAMPLE 8

2-trans-n-butyl-5-/4'-isothiocyanatophenyl/-1,3-dioxane

Following the preceding scheme 4 the compound of m.p. 74.5° C. was obtained.

EXAMPLE 9

2-trans-n-octyl-5-/4'-isothiocyanatophenyl/-1,3-dioxane

Following the procedure described in Example 8 the compound of m.p. 84° C. was obtained.

The compounds of the formula I are useful to make liquid crystalline admixtures for electrooptical devices. The compounds of the formula I preferred for that purpose are those wherein the symbols X stand for carbon atom bonded with two hydrogen atoms /—$CH_2$— group/, the symbols Z stand for oxygen atom, R represents alkyl or 4-alkylphenyl group whereas m is an integer of 1. The prefered alkyl groups are those of straight alkyl chain containg from 2 to 12 atoms of carbon or branched alkyl $C_2H_5$—CH/$CH_3$/—/$CH_2$/$_k$ wherein k in integer of 1, 2 or 3.

The following are examples of preferred compounds of formula I:

trans-5-ethyl-2-/4'-isothiocyanatophenyl/-1,3-dioxane
trans-5-n-propyl-2-/4'-isothiocyanatophenyl/-1,3-dioxane
trans-5-n-butyl-2-/4'-isothiocyanatophenyl/-1,3-dioxane
trans-5-n-pentyl-2-/4'-isothiocyanatophenyl/-1,3-dioxane
trans-5-n-hexyl-2-/4'-isothiocyanatophenyl/-1,3-dioxane
trans-5-n-heptyl-2-/4'-isothiocyanatophenyl/-1,3-dioxan
trans-5-n-octyl-2-/4'-isothiocyanatophenyl/-1,3-dioxane
trans-5-n-nonyl-2-/4'-isothiocyanatophenyl/-1,3-dioxane
trans-5-n-decyl-2-/4'-isothiocyanatophenyl/-1,3-dioxane
trans-5-n-undecyl-2-/4'-isothiocyanatophenyl/-1,3-dioxane
trans-5-n-duodecyl-2-/4'-isothiocyantophenyl/-1,3-dioxane
trans-5-/2-methylbutyl/-2-/4'-isothiocyanatophenyl/-1,3-dioxane
trans-5-/3-methylpentyl/-2-/4'-isothiocyanatophenyl/-1,3-dioxane
trans-5-/4-methylhexyl/-2-/4'-isothiocyanatophenyl/-1,3-dioxane
trans-5-/4'-ethylphenyl/-2-/isothiocyanatophenyl/-1,3-dioxane
trans-5-/4'-n-propylphenyl/-2-/isothiocyanatophenyl/-1,3-dioxane
trans-5-/4'-butylphenyl/-2-/isothiocyanatophenyl/-1,3-dioxane
trans-5-/4'-n-pentylphenyl/-2-/isothiocyanatophenyl/-1,3-dioxane
trans-5-/4'-n-hexylphenyl/-2-/isothiocyanatophenyl/-1,3-dioxane
trans-5-/4'-n-heptylphenyl/-2-/isothiocyanatophenyl/-1,3-dioxane
trans-5-/4'-n-octylphenyl/-2-/isothiocyanatophenyl/-1,3-dioxane trans-5-[4'-/2-methylbutyl/phenyl]-2-/isothiocyanato-phenyl/-1,3-dioxane There is possible to prepare liquid crystalline nematic substances by mixing of the selected compounds of the formula I having smectic A phases with one or several liquid crystalline compounds containg cyano, nitro or aldehyde groups at the terminal position of the molecule of the structure expressed by formulae II–XI:

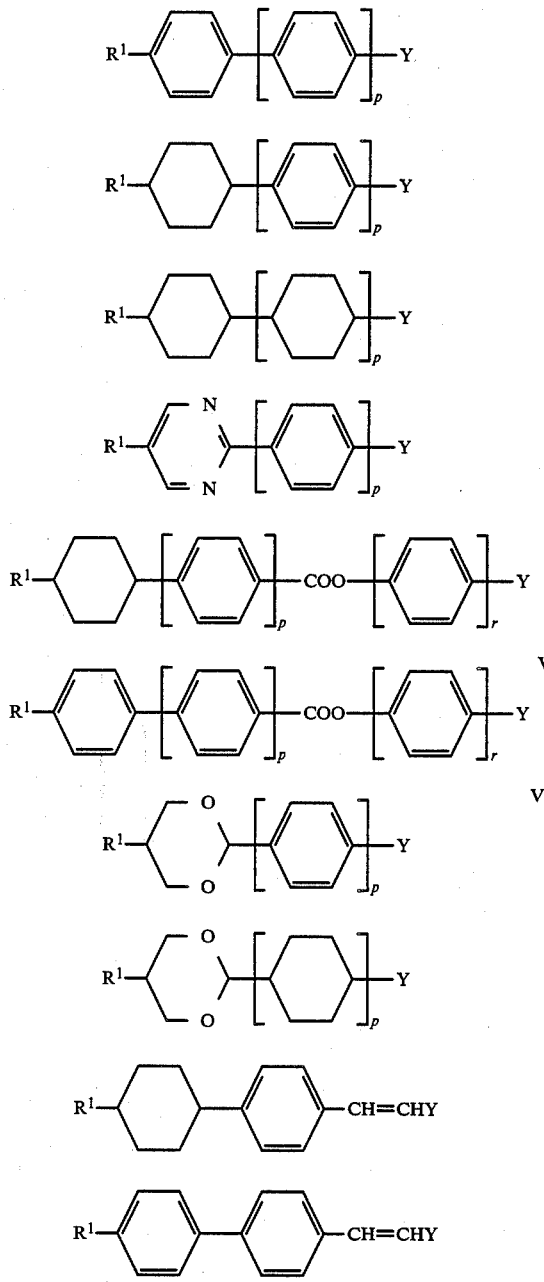

wherein p and r are an integer of 1 or 2, R represents alkyl, alkoxy, alkanoyloxy, alkylcarbonate ($H_{2n+1}OCOO$) or alkylphenyl group, and akyl groups contain from 1 to 15 carbon atom within the chain, which may be straight or branched. The symbol Y stands for nitro, cyano or aldehyde group. The nematic admixture of low melting point is prepared by mixing at least one compound of the formula I /in which $R=H_{2n+1}C_n$, X stands for a carbon atom bonded with two hydrogen atoms, Z stands for an oxygen atom, m=1/ with at least one compound of formulae II–XI /in which p and r=1; Y stands for cyano or nitro group/.

If mentioned compounds of formulae II–XI have smectic phases it is advantageous to mix them with the compound of the formula I in which n at the terminal group R is from 1 to 8 so that the ratio of smectic layer spacings of compiounds of the formulae II–XI to I, is greater or equal 1.2, and concentration of compounds of the formulae II–XI, is changed within 40–90% of moles. In this concentrations range it is possible to obtain liquid crystalline admixtures of nematic properties, whereas in the remaining concentration area those of smectic or simultaneously nematic and smectic properties as shown on phase diagram, FIG. 1, which relates to the admixture consisting of 5-trans-n-butyl-2-/4'-isothiocyanatophenyl/-1,3-dioxane /called the compound A/ and 4-octyloxy-4'-cyanobiphenyl /called the compound B/. The diagram symbols represent as follows: I, $S_A$, N, Cr—respectively isotropic phase, smectic A phase, nematic phase, crystalline solid phase. An addition of the compound B to the compound A results in gradual reduction of smectic $S_A$ phase stability of the component A. At the concentration of about 10 mole % of B the nematic phase appears in admixture and its range of existence is increased systematically even at the concentration greater than 50 mole % of B, up to the concentration 90 mole % of B only the nematic phase exists.

If the component A is added to the component B, stability of smectic phase of the component B is dramaticaly decreased and is not observed in the mixture containing 10 mole % of the component A. The area of smectic phase of the component A is separated from that of the component A by the nematic gap. Within the range of component A concentrations from 45 to 10 mole % there is observed only the nematic phase within the whole range of temperatures in which this admixture is observed in mesomorphic state. The nematic phase as a stable state is observed in this binary system within the relatively narrow range of temperatures 30°–70° C., but when the admixture is prepared from more than two components it is possible to enhance the nematic temperature range if only the ratio of components A and B is maintained within the mentioned above range determining the width of the nematic gap. Admixtures prepared according to the mentioned above procedure from the compounds of formula I as well as II–XI, wherein m or p and r=1 have usually low clarification points within the range 40°–50° C.; and for increase of those temperatures it is possible to add from several to a dozen or so percents of the compounds of the formulae II–XI, in which p or r=2, or esters of the formula VI, in which p and r=1, whereas Y=F, Cl, Br, I, $COCH_3$, NCS, or other compounds e.g. the derivatives of dioxane of formulae XII–XIII in which q=2–8, $R^1$ stands for alkyl /$H_{2n+1}C_n$/.

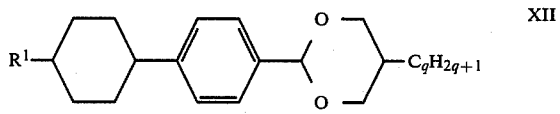

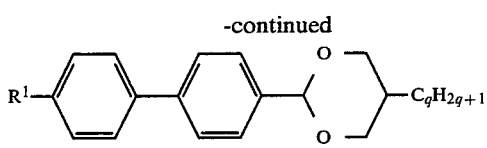

$$\text{R}^1-\underset{}{\underset{}{\bigcirc}}-\underset{}{\underset{}{\bigcirc}}-\underset{O}{\overset{O}{\underset{\diagdown}{\diagup}}}C_qH_{2q+1} \quad \text{XIII}$$

For facilitation of nematic layer arrangement in the cell a crystalline admixture should contain a small amount /less than 1 mole %/ of an optically active compound, for instance the compound of the formula I, in which R=C$_2$H$_5$CH/CH$_3$/—CH$_2$— or C$_2$H$_5$CH/CH$_3$/CH$_2$O— or the compound of the formulae II–XI, in which R stands for the same, or any cholesterol derivative. The addition of an optically active compound may come up to tens percents to obtain the admixtures showing the electric field-induced cholesteric—nematic phase transition.

Properties of liquid crystalline nematic substances may be also modified by introducing liquid crystalline compounds of a small negative dielectric anisotropy, e.g. alkyl or alkoxybenzoate esters, alkyl or alkoxyphenyl derivatives of dioxane and azoxy compounds. Smectic liquid crystalline admixtures may be obtained by mixing the compounds of the formula I among them. The admixtures obtained from several compounds of the formula I, in which m=1 are characterized by low melting points. An addition of compounds of the formula I, wherein R=H$_{2n+1}$C$_n$C$_6$H$_4$ or m=2 to such a liquid crystalline substance results in an increase of clarification point. In order to attain smectic admixture, which has the nematic phase within the upper range of the mesophase near the clarification point, several or dozen or so percents of the compounds of the formulae II–XI are added to the admixture prepared froom those of the formula I. The greater participation of the compounds of the formulae II–XI takes place in the admixtures obtained from the compounds of the formula I, the greater the nematic gap occurs between smectic and isotropic phase. The usage of the compounds being the subject of the present invention for preparation of liquid crystalline admixtures of various properties is illustrated by the examples mentioned below.

Preparation of nematic admixtures from compounds having smectic phases.

EXAMPLE 10

The admixture of the following mole % content from two smectic compounds was prepared:

| | |
|---|---|
| 5-trans-n-butyl-2-/4'-isothiocyanatophenyl/-1,3-dioxane | 40 |
| of the phase transition temperatures Cr 60 S$_A$ 75 I | |
| 4-octyloxy-4'-cyanobiphenyl | 60 |
| of the phase transition temperatures Cr 54.5 S$_A$ 67 N 80 I | |

The admixture of that content had only the neamtic phase from the melting point 40° C. to the clarification point 60° C. This admixture might be overcooled to 20° C. and up to this temperature only the nematic phase was observed. If 10 mole % of 4-cyano-4'-pentylterphenyl was added to that binary admixture the increase of the clarification point up to 83° C. was obtained as well as the decrease of the melting point down to 36° C. This three-components system might be overcooled to 10° C. and up to this temperature only nematic phase was observed.

The nematic admixture may be also prepared from compounds having only smectic phase in the following way:

| | |
|---|---|
| 5-trans-n-hexyl-2-/4'-isothiocyanatophenyl/-1,3-dioxane | 65 |
| Cr 35 S$_A$ 79 I | |
| 4-dodecyloxy-4'-cyanobiphenyl | 35 |
| Cr 69 S$_A$ 89.5 I | |

The admixture of that composition has nematic phase from the melting point 50° C. to the clarification point 67° C. The smectic phase was not observed after supercooling to 10° C.

If the admixture was prepared from two or more compounds of the formula I and two or more compounds determined by the formulae II–XI the nematic phase was obtained at more advantageous temperatures range for practical purposes, which is illustrated by the examples.

EXAMPLE 11

The quaternary admixture of weight % content was prepared as follows:

| | |
|---|---|
| 5-trans-n-butyl-2-/4'-isothiocyanatophenyl/-1,3-dioxane | 18 |
| Cr 60 S$_A$ 75 I | |
| 5-trans-n-hexyl-2-/4'-isothiocyanatophenyl/-1,,3-dioxane | 30 |
| Cr 35 S$_A$ 79 I | |
| 4-/trans-4'-n-pentylcyclohexyl/-1-/2-cyanovinyl/benzene | 19 |
| Cr 48.5 S$_A$ 61 N 149.5 I | |
| 4-/trans-4'-n-heptylcyclohexyl/-1-/2-cyanovinyl/benzene | 33 |
| Cr 39 S$_A$ 120 N 143.5 I | |

This composition clarified at 99° C., melted at −4° C. and had only the nematic phase within the whole range of temperatures. If the system had behaved additively a smectic—nematic phase transition at 87.5° C. should have been observed. To this composition 1 weight % of dichroic dye D35 /of BDH production/ was added and the liquid crystalline admixture of bluepurple colour was obtained useful to display colourless symbols or digits on a coloured background or coloured symbols or digits on a colourless background depending on construction and the manner of control of the liquid crystalline cell.

The nematic admixture from compounds having a smectic phase and those having a nematic one.

EXAMPLE 12

The binary system composed of smectic and nematic compounds was prepared of content in mole %.

| | |
|---|---|
| 5-trans-n-butyl-2-/4'-isothiocyanatophenyl/-1,3-dioxane | 50 |
| Cr 60 S$_A$ 75 I | |
| 5-trans-n-hexyl-2-/4'-cyanophenyl/-1,3-dioxane | 50 |
| Cr 48.5 N /43/ I | |

This system had only the nematic phase within the whole range of the temperatures in which it exists in a mesomorphic phase.

EXAMPLE 13

The ternary admixture containing in weigh % was prepared:

| | |
|---|---|
| 4-/trans-4'-propylcyclohexyl/-1-isothiocyanatobenzene | 30 |
| Cr 38.5 N 44.5 I | |

-continued

| | |
|---|---|
| 4-/trans-4'-hexylcyclohexyl/-1-isothiocyanatobenzene<br>Cr 12.5 N 43 I | 40 |
| 5-trans-n-hexyl-2-/4'-isothiocyanatophenyl/-1,3-dioxane<br>Cr 35 $S_A$ 79 I | 30 |

This composition clarified at 40° C., it had a nematic phase up to −20° C., its dielectric anisotropy at 20° C. $\Delta\epsilon = \epsilon_\parallel - \epsilon_\perp$ was +6.5.

If 10 weight % of 4''-nitrophenyl-4-/trans-4'-butylcyclohexyl/benzoate was added to that admixture the temperature of the namatic-isotropic phase transition was increased up to 53° C.

EXAMPLE 14

The ternary admixture was prepared containing in weight %:

| | |
|---|---|
| 4-/trans-4'-propylcyclohexyl/-1-isothiocyanatobenzene<br>Cr 38.5 N 41.5 I | 30 |
| 4-/trans-4'-hexylcyclohexyl/-1-isothiocyanatobenzene<br>Cr 12.5 N 49 I | 40 |
| 5-trans-/2-methylbutyl/-2-/4'-isothiocyanatophenyl/-1,3-dioxane<br>Cr 53.5 $S_A$ /47.5/ I | 30 |

This mixture was cholesteric and showed the cholesteric-nematic phase transition after electric field had been supplied.

EXAMPLE 15

The six components admixture was prepared containing in weight %:

| | |
|---|---|
| 4-/trans-4'-propylcyclohexyl/-1-isothiocyanatobenzene | 28 |
| 4-/trans-4'-n-hexylcyclohexyl/-1-isothiocyanatobenzene | 29.4 |
| 4-/trans-4'-n-octylcyclohexyl/-1-isothiocyanatobenzene | 12.6 |
| 5-trans-n-hexyl-2-/4'-isothiocyanatophenyl/-1,3-dioxane | 15 |
| 5-trans-/4'-n-propylphenyl/-2-/4''-isothiocyanatophenyl/-1,3-dioxane | 5 |
| 5-trans-n-butyl-2-/4'-/4''-trans-n-pentylcyclohexyl/phenyl]-1,3--dioxane | 10 |

This admixture clarified at 57° C., it was in nematic form, its dielectric anisotropy $\Delta\epsilon = \epsilon_{11} - \epsilon_\perp$ at 20° was +6.8. Treshold tension at 20° C. was 1.6 and the saturation tension was 2.3.

Nematic admixtures and smectic admixtures of the narrow nematic phase range near the clarification point.

EXAMPLE 16

The binary admixture was prepared the following compounds in mole %:

| | |
|---|---|
| 5-trans-n-butyl-2-/4'isothiocyanatophenyl/-1,3-dioxane<br>Cr 60 $S_A$ 75 I | 55 |
| 5-trans-n-hexyl-2-/4'-isothiocyanatophenyl/-1,3-dioxane<br>Cr 39 $S_A$ 79 I | 45 |

This binary mixture had only the smectic A phase and the clarification point 75° C. It was easily overcooled which allowed observation of the smectic phase at temperatures lower than 0° C.

EXAMPLE 17

The clarification point of the admixture of example 16 might be decreased by an addition of 5-trans-ethyl-2-/4'-isothiocyanatophenyl/-1,3-dioxane which has lower clarification point then other compounds from the series. The ternary admixture composed of:

| | |
|---|---|
| 5-trans-ethyl-2-/4'-isothiocyanatopfenyl/-1,3-dioxane<br>Cr 70 $S_A$ /50/ I | 33.3 mole % |
| 5-trans-n-butyl-2-/4'-isothiocyanatophenyl/-1,3-dioxane<br>Cr 60 $S_A$ 75 I | 33.3 mole % |
| 5-trans-n-hexyl-2-/4'-isothiocyanatophenyl/-1,3-dioxane<br>Cr 35 $S_A$ 74 I | 33.3 mole % | has its transition temperature from a smectic to an isotropic phase at 62° C. and transition temperature from a crystalline phase to a smectic A one −2° C. Further decrease of the $S_A \rightarrow I$ transition temperature might be achieved by an addition of any bi-ringed liquid crystalline compounds of the formulae II–XII at terminal position of the molecule a group Y=CN; NO2 or NCS where m=1 and p=1 in amounts 5–10% by weight.

EXAMPLE 18

4-/trans-4'-n-propylcyclohexyl/-1-isothiocynatobenzene /Cr 38.5N 41.5 I/ in amount 5 weight % was added to the three components admixture from example 17 which had the $S_A \rightarrow I$ transition temperature 62° C. Thus the admixture was obtained having the $S \rightarrow I$ temperature 58.5° C., on the other hand, if 10 weight % of that compound was added and the system was heated up to the temperature over the clarification point and then cooled, the transition to N and $S_A$ phase at 51° C. was simultaneously observed and both phases coexisted in equilibrium up to 46° C., below this temperature the admixture is smectic. If 15 weight % of 4-/trans-4'-n-propylcyclohexyl/-1-isothiocyanatobenzene was added to the ternary admixture from example 17 and the mixture was heated until it was clarified and then cooled, the observation was made as follows: the mixture was nematic at 49° C., it turned gradually to the smectic phase at 47° C. and had only the smectic phase at 42° C.

We claim:

1. Compounds of the general formula:

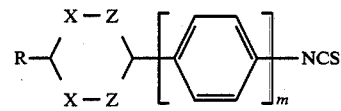

I wherein the symbols X stand for a carbon atom bonded with two hydrogen atoms /—CH2— group/ and the symbols Z stand for oxygen atom or the symbols X stand for oxygen atom or the symbols Z stand for a carbon atom bonded with two hydrogen atoms /—CH2— group/, m is an integer of 1 to 2, R represents an alkyl /H$_{2n+1}$C$_n$—/ or an 4-alkylphenyl /H$_{2n+1}$C$_n$C$_6$H$_4$—/ group, the term alkyl group signifies an alkyl chain containing 1 to 15 carbon atoms and the chain is straight or branched.

2. Compounds as claimed in claim 1 where the symbols X stand for carbon atom bonded with two hydrogen atoms /—CH2— group/ and the symbols Z stand for oxygen atom, m is the integer of 1 and R represents an alkyl or an alkylphenyl group.

3. Compounds as claimed in claim 2 where R represents normal alkyl group.

4. Compounds as claimed in claim 2 where R represents a branched alkyl group, C$_2$H$_5$—CH/CH$_3$/—/CH$_2$/$_k$, k is an interger of 1 to 3.

5. A liquid crystalline admixture containing at least two liquid crystalline components, wherein at least one component is a compound of the formula I as claimed in claim 1.

6. The liquid crystalline admixture as claimed in claim 5, which contains one or more liquid crystalline compounds of formula I defined in claim 1 and one or more compounds of the formulae:

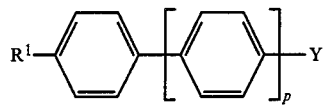  II

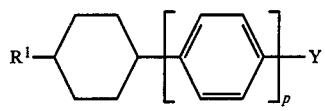  III

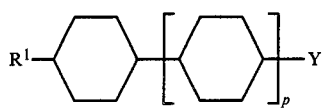  IV

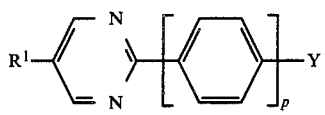  V

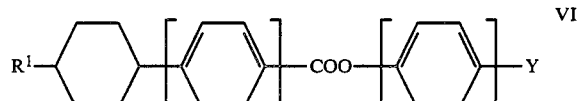  VI

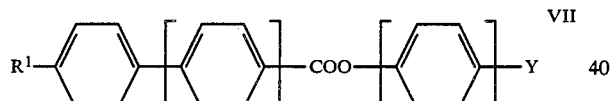  VII

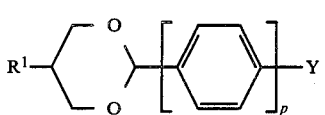  VIII

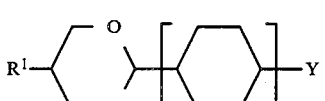  IX

  X

  XI wherein symbols p and r are the integer of 1 to 2, Y represents NO$_2$ or CN group, R$^1$ represents an alkyl, an alkoxy, an alkylcarbonate, an alkoxycarboxy, an alkylphenyl group.

7. The liquid crystalline admixture as claimed in claim 6, which contains 50 to 90 percent by weight of at least one of the compounds of the formulae II to XI defined in claim 6, wherein R$^1$ represents an alkyl or an alkoxy group having at least 5 carbon atom in the alkyl chain, p is the integer of 1.

8. A liquid crystalline admixture as claimed in claim 5, which additionally contains an optically active dopant compound and/or a pleochroic or dichroic dye.

9. A liquid crystalline admixture containing as liquid crystalline components at least two of the compounds of formula I as claimed in claim 2.

10. A liquid crystalline admixture as claimed in claim 9 containing at least two compounds of the formula I, wherein R represents an alkyl group in which at least one of said compounds from the group having alkyl groups containing from 2 to 6 carbon atoms and at least one of said compounds is selected from the groups containing from 8 to 12 carbon atoms both of said groups being present simultaneously in said admixture.

11. A method for the preparation of nematic liquid crystalline mixtures from smectic compounds which comprises the steps of adding to at least one compound selected from the compounds according to claim 1 or mixtures thereof, at least one compound selected from the group of compounds having the formulae II through XI

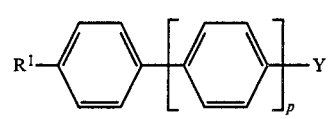  II

  III

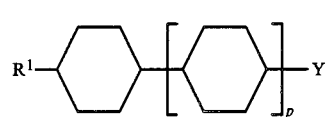  IV

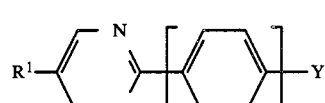  V

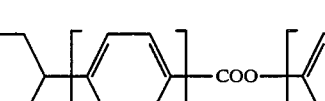  VI

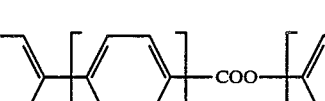  VII

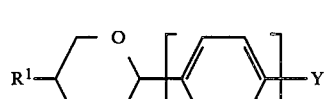  VIII

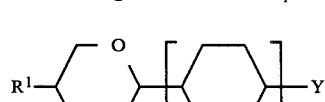  IX

-continued

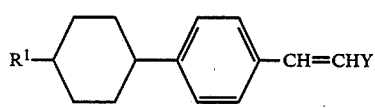 X

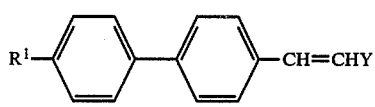 XI wherein
p and r are the integer 1 or 2;
Y is NO$_2$ or CN;
R$^1$ is alkyl, alkoxy, alkanoyloxy, alkylcarbonato or alkylphenyl.

12. The method for the preparation of nematic phase mixtures according to claim 11 wherein 50 to 90 wt.% of a compound selected from the group having the formulae II to XI, wherein R$^1$ is alkyl or alkoxy with at least 5 carbon atoms in said alkyl portion, and p is 1; is admixed to at least one compound having the formula I.

* * * * *

Adverse Decision in Interference

In Intererence No. 102,348, involving Patent No. 4,676,924, R. Dabrowski, J. Dziaduszek, J. Szulc, Z. Witkiewicz, Z. Stolarz, K. Kenig G. Adamska, LIQUID CRYSTALLINE ISOTHIOCYANATES WITH DIOXANE RING AND LIQUID CRYSTALLINE ADMIXTURES CONTAINING SAME, final judgment adverse to the patentees was rendered June 25, 1990, as to claims 1-12.

*[Oficial Gazette August 28, 1990]*